United States Patent [19]

Bender et al.

[11] 4,005,208

[45] Jan. 25, 1977

[54] N-HETEROCYCLIC-9-XANTHENYLAMINES

[75] Inventors: Paul E. Bender, Willingboro, N.J.;
Bernard Loev, Broomall, Pa.

[73] Assignee: SmithKline Corporation,
Philadelphia, Pa.

[22] Filed: May 16, 1975

[21] Appl. No.: 578,226

[52] U.S. Cl. .......................... 424/267; 260/293.58;
260/326.5 CA; 424/274
[51] Int. Cl.² ...................................... C07D 405/12
[58] Field of Search ............ 260/293.58, 326.5 CA;
424/267, 274

[56] References Cited

UNITED STATES PATENTS 3,558,779  1/1971  Adams et al. ..................... 424/283

*Primary Examiner*—G. Thomas Todd
*Attorney, Agent, or Firm*—Joan S. Keps; Richard D. Foggio; William H. Edgerton

[57] ABSTRACT

The compounds are N-piperidinyl and pyrrolidinyl-9-xanthenylamines which are inhibitors of gastric acid secretion.

6 Claims, No Drawings

N-HETEROCYCLIC-9-XANTHENYLAMINES

This invention relates to new N-heterocyclic-9-xanthenylamines, in particular to N-piperidinyl and pyrrolidinyl-9-xanthenylamines, having pharmacological activity. These compounds inhibit gastric acid secretion.

The compounds of this invention are represented by the following formula:

FORMULA I

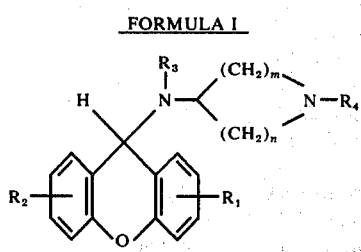

in which:
R$_1$ is hydrogen, halogen, hydroxy, lower alkyl or lower alkoxy;
R$_2$ is hydrogen, halogen, lower alkyl or lower alkoxy;
R$_3$ is hydrogen or lower alkyl;
R$_4$ is hydrogen, lower alkyl, allyl, propargyl, cycloalkyl having 3 to 6 carbon atoms, lower alkanoyl, lower alkoxycarbonyl, carbamoyl, N-lower alkylcarbamoyl, N,N-di-lower alkylcarbamoyl, phenyl or benzyl;
$m$ is 1 or 2 and $n$ is 2 or 3, the sum of $m$ and $n$ being 3 or 4 or a pharmaceutically acceptable acid addition salt thereof.

Preferably, in compounds of Formula I, R$_1$ and R$_2$, being the same or different, are hydrogen, chloro, methyl or methoxy.

Particularly preferred compounds of this invention are represented by Formula I in which R$_1$ and R$_2$ are hydrogen, R$_3$ is hydrogen or methyl and R$_4$ is methyl or ethyl.

An advantageous compound of this invention is N-(N-ethyl-3-piperidinyl)-9-xanthenylamine.

When $m$ is 1 and $n$ is 2 or 3, that is when the heterocyclic ring is attached to the amino group at the 3-position or when R$_1$ and R$_2$ are different, compounds may exist as the d or l isomers. These isomers as well as the dl mixtures thereof are included within this invention.

The compounds of this invention produce inhibition of gastric acid secretion. This activity is demonstrated by administration to pylorus ligated rats at doses of about 30 to 50 mg./kg. orally and at about 5 to 50 mg./kg. intraduodenally. Also, this activity is demonstrated by administration to chronic gastric fistula rats at doses of about 25 mg./kg. orally and to chronic gastric fistula monkeys at doses of about 1.9 to 15 mg./kg. by intragastric administration. In these procedures, compounds which produce an increase in gastric pH or a decrease in volume of gastric juice or both are considered active.

These compounds show antiulcer activity, for example in the restraint-stress method in which on oral administration to rats at doses of about 7.5 to 30 mg./kg. these compounds inhibit the development of experimental ulcers.

These compounds which inhibit gastric acid secretion are useful in treating gastric and duodenal ulcer disease and other conditions involving gastric acid hypersecretion.

The compounds of this invention are prepared by the following procedures:

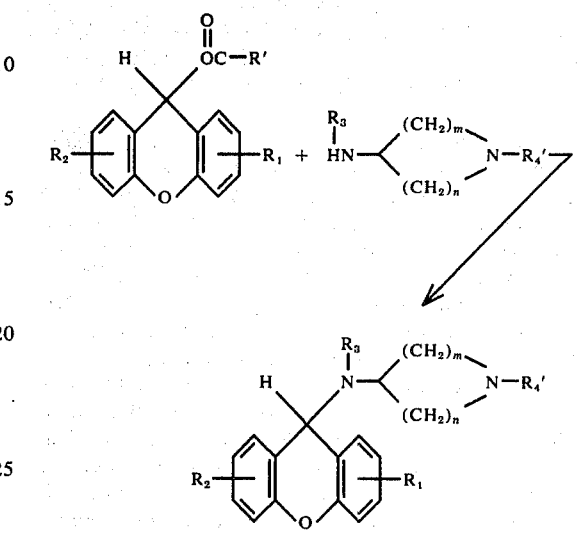

The terms R$_1$–R$_3$, $m$ and $n$ are as defined above, R$_4'$ is lower alkyl, allyl, propargyl, cycloalkyl having 3 to 6 carbon atoms, lower alkanoyl, lower alkoxycarbonyl, carbamoyl, N-lower alkylcarbamoyl, N,N-di-lower alkylcarbamoyl, phenyl or benzyl and R' is lower alkyl, preferably methyl.

According to the above procedure, a 9-xanthenyl alkanoate is reacted with an aminopiperidine or pyrrolidine. The reaction is preferably carried out in an inert solvent such as benzene or toluene, at elevated temperature, conveniently at reflux temperature.

The compounds of Formula I in which R$_4$ is hydrogen are prepared by treating the corresponding compounds in which R$_4$ is lower alkoxycarbonyl, such as ethoxycarbonyl or a benzoyl group with base such as potassium hydroxide in aqueous ethanol.

The 9-xanthenyl alkanoate starting materials are either known to the art or are prepared from xanthydrols by reacting with a lower alkyl isocyanate to give a 9-lower alkylcarbamoyloxyxanthene and reacting that intermediate with a lower alkanoic acid.

The xanthydrols are either known to the art or are prepared by the following procedure. A 2-halobenzoic acid is reacted with a phenol preferably in the presence of a base such as potassium carbonate and in the presence of cuprous iodide and copper bronze. The resulting 2-phenoxybenzoic acid is cyclized by treating with acid for example polyphosphoric acid. The resulting xanthone is reduced, for example using sodium amalgam in ethanol, to give the xanthydrol.

The amino-1-R$_4'$-piperidine and pyrrolidine starting materials are either known to the art or are prepared by known procedures. For example, they are prepared by reductive amination of the corresponding N-R$_4'$-piperidones or pyrrolidinones. The appropriate substituted piperidones and pyrrolidinones are either known to the art or are prepared by known procedures such as N-alkylating or N-acylating a N-unsubstituted piperidone or pyrrolidinone or by cyclizing a N-substituted-N-

(lower alkoxycarbonyl-$(CH_2)_m$)-N-(lower alkoxycarbonyl-$(CH_2)_m$)-amine.

Also, 1-substituted 3-aminopyrrolidine starting materials are prepared by reacting a substituted amine with 1,4-dibromo-2-butanol at elevated temperature to give 1-substituted-3-pyrrolidinol which is treated with hydrochloric acid and thionyl chloride to give the 3-chloropyrrolidine. This intermediate is reacted with potassium phthalimide in dimethyl sulfoxide and the resulting 1-substituted-3-phthalimidopyrrolidine is reacted with hydrazine hydrate to give the 1-substituted-3-aminopyrrolidine.

Also, 1-substituted aminopiperidine and pyrrolidine starting materials are prepared by reacting a 1-unsubstituted aminopiperidine or aminopyrrolidine with two equivalents of phthalic anhydride to give 1-(2-carboxylbenzoyl)phthalimidopiperidine or pyrrolidine; removing the 1-substituent by treating with hydrochloric acid, N-alkylating or acylating to give the 1-substituted phthalimidopiperidine or pyrrolidine and reacting with hydrazine hydrate to remove the phthaloyl group.

The pharmaceutically acceptable, acid addition salts of the compounds of Formula I are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric, and nitric acids. Of course, these salts may also be prepared by the classical method of double decomposition of appropriate salts which is well-known to the art.

Preferably, the compounds are administered in conventional dosage forms prepared by combining an appropriate dose of the compound with standard pharmaceutical carriers.

Pharmaceutical compositions having gastric acid secretion inhibitory activity, in dosage unit form, comprising a pharmaceutical carrier and a gastric acid secretion inhibiting amount of a compound of Formula I or a pharmaceutically acceptable acid addition salt thereof are objects of this invention.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The methods of inhibiting gastric acid secretion in accordance with this invention comprise administering internally to an animal an effective amount of a compound of Formula I or a pharmaceutically acceptable acid addition salt thereof. The active ingredients will preferably be administered in dosage unit form as described above.

The compounds of this invention will be administered in a daily dosage regimen of from about 10 mg. to about 2 g., preferably from about 25 mg. to about 1 g. Advantageously, equal doses will be administered one to four times per day. Dosage units will contain from about 10 mg. to about 500 mg., preferably from about 25 mg. to about 300 mg., of the active ingredient.

When administration is carried out as described above, gastric acid secretion is inhibited.

One skilled in the art will recognize that in determining the amounts of the active ingredients in the claimed compositions and used in the claimed methods, the activity of the chemical ingredient as well as the size of the host animal must be considered.

The terms "lower alkyl" and "lower alkoxy" where used herein denote groups having, preferably, 1–4 carbon atoms; "lower alkanoyl" denotes groups having, preferably, 2–4 carbon atoms and "halogen" denotes chloro, bromo or fluoro.

The following examples are not limiting but are illustrative of the invention.

EXAMPLE 1

Methyl isocyanate (20 g.) was added slowly, with stirring, to a filtered solution of 30 g. of xanthydrol in 100 ml. of anhydrous triethylamine. After standing for 40 minutes in a 20° C. water bath, the mixture was filtered. The collected solid was washed with anhydrous diethyl ether and dried in vacuo to give 9-(N-methylcarbamoyloxy)xanthene.

To 15 g. of 9-(N-methylcarbamoyloxy)xanthene, suspended in 200 ml. of dry ether, was added 18 ml. of glacial acetic acid with stirring. After one hour, the lower acid layer was removed. The ether phase was then cooled, neutralized with cold aqueous sodium bicarbonate, dried over anhydrous magnesium sulfate and concentrated in vacuo. The residue was recrystallized from benezene-hexane to give 9-acetoxyxanthene, m.p. 109°–112° C.

A solution of 4.0 g. of 9-acetoxyxanthene and 2.36 g. of 3-amino-1-ethylpiperidine in 175 ml. of dry toluene was refluxed for 24 hours. The cooled solution was then concentrated in vacuo. The residue was chromatographed on activated magnesium silicate, eluting with ether and acetone. Concentration of the acetone fraction in vacuo and then chromatographing on silica gel with acetone, then concentrating the eluate in vacuo gave N-(N-ethyl-3-piperidinyl)-9-xanthenylamine, m.p. 47.5°–48.5° C.

EXAMPLE 2

A suspension of 0.25 g. of platinum dioxide in 20 ml. of methanol was shaken under 30 p.s.i. of hydrogen for one hour. To this activated catalyst was added a solution of 7.9 g. (48 mmoles) of 1-ethyl-3-piperidone and 3.1 g. (100 mmoles) of methylamine in 40 ml. of methnol. This mixture was shaken under about 50 p.s.i. of hydrogen for 1.5 hours, then filtered. The solvent was distilled off the filtrate at atmospheric pressure. The residue was then distilled at reduced pressure to give 1-ethyl-3-methylaminopiperidine, b.p. 88°–90.5° C. at 28 mm.

A solution of 3.7 g. (15.4 mmoles) of 9-acetoxyxanthene and 2.2 g. (15.5 mmoles) of 1-ethyl-3-methylaminopiperidine in 80 ml. of benzene was refluxed under nitrogen for 22.5 hours. It was then cooled to room temperature, washed with aqueous sodium bicarbonate solution, and dried over potassium carbonate. After removal of solvent in vacuo, the residue was dissolved in 25 ml. of petroleum ether and filtered from a small amount of crystals. The filtrate was then concentrated in vacuo and chromatographed on silica gel (ether solvent) to give N-methyl-N-(N-ethyl-3-piperidinyl)-9-xanthenylamine.

EXAMPLE 3

A solution of 4.0 g. of 9-acetoxyxanthene and 1.9 g. of 4-amino-1-methylpiperidine in 100 ml. of dry benzene was refluxed for 24 hours. The cooled solution was then washed with 5% aqueous sodium carbonate solution and the organic layer was dried over anhydrous sodium sulfate, filtered and concentrated in vacuo. The residue crystallized on triturating with hexane and was recrystallized from hexane to give N-(N-methyl-4-piperidinyl)-9-xanthenylamine, m.p. 96.5°–98° C.

EXAMPLE 4

By the procedure of Example 1, using 3-amino-1-methylpiperidine in place of 3-amino-1-ethylpiperidine, the product is N-(N-methyl-3-piperidinyl)-9-xanthenylamine.

EXAMPLE 5

By the procedure of Example 2, using the following alkylamines in place of methylamine:
 ethylamine
 propylamine
 butylamine
the following products are obtained, respectively:
 N-ethyl-N-(N-ethyl-3-piperidinyl)-9-xanthenylamine
 N-propyl-N-(N-ethyl-3-piperidinyl)-9-xanthenylamine
 N-butyl-N-(N-ethyl-3-piperidinyl)-9-xanthenylamine.

EXAMPLE 6

Refluxing 4.0 g. of 9-acetoxyxanthene and 2.05 g. of 3-amino-1-ethylpyrrolidine in 175 ml. of dry toluene for 24 hours, then working up as in Example 1 gives N-(N-ethyl-3-pyrrolidinyl)-9-xanthenylamine.

EXAMPLE 7

To 55.8 g. of 1-cyclohexyl-4-piperidine on 40 ml. of absolute ethanol with 4 ml. of Raney nickel catalyst in a cooled bomb is added 55 ml. of liquid ammonia. The bomb is charged at a pressure of 2,900 p.s.i. of hydrogen and then heated to 150° C. with shaking for 20 minutes. After cooling to 25° C., the mixture is filtered and the solid washed with dry ether. The combined filtrates are concentrated in vacuo and the residue distilled to give 4-amino-1-cyclohexylpiperidine.

Refluxing 4-amino-1-cyclohexylpiperidine and 9-acetoxyxanthene in dry toluene for 24 hours, then working up as in Example 1 gives N-(N-cyclohexyl-4-piperidinyl)-9-xanthenylamine.

EXAMPLE 8

By the procedure of Example 7, using in place of 1-cyclohexyl-4-piperidone, the following 1-substituted pyrrolidinones:
 1-methyl-3-pyrrolidinone
 1-butyl-3-pyrrolidinone
the products are, respectively:
 N-(N-methyl-3-pyrrolidinyl)-9-xanthenylamine
 N-(N-butyl-3-pyrrolidinyl)-9-xanthenylamine.
Similarly, using the following piperidones in the procedure of Example 7:
 1-benzyl-4-piperidone
 1-propyl-4-piperidone
 1-butyl-4-piperidone
the products are, respectively:
 N-(N-benzyl-4-piperidinyl)-9-xanthenylamine
 N-(N-propyl-4-piperidinyl)-9-xanthenylamine
 N-(N-butyl-4-piperidinyl)-9-xanthenylamine.

EXAMPLE 9

Reductive amination of 1-phenyl-3-piperidone by the procedure of Example 7 gives 3-amino-1-phenylpiperidine.

Refluxing 3-amino-1-phenylpiperidine with 9-acetoxyxanthene in dry toluene by the procedure of Example 1 gives N-(N-phenyl-3-piperidinyl)-9-xanthenylamine.

Also, by the procedure of Example 1, using 2-chloroxanthydrol as a starting material and reacting the intermediate 9-acetoxy-2-chloroxanthene with 3-amino-1-phenylpiperidine, the product obtained is N-(N-phenyl-3-piperidinyl)-2-chloro-9-xanthenylamine.

EXAMPLE 10

By the procedure of Example 1, using in place of xanthydrol the following:
 2-chloroxanthydrol
 3-chloroxanthydrol
 4-chloroxanthydrol
 1-chloroxanthydrol
 3-fluoroxanthydrol
 2-bromoxanthydrol
the following products are obtained, respectively:
 N-(N-ethyl-3-piperidinyl)-2-chloro-9-xanthenylamine
 N-(N-ethyl-3-piperidinyl)-3-chloro-9-xanthenylamine
 N-(N-ethyl-3-piperidinyl)-4-chloro-9-xanthenylamine
 N-(N-ethyl-3-piperidinyl)-1-chloro-9-xanthenylamine
 N-(N-ethyl-3-piperidinyl)-3-fluoro-9-xanthenylamine
 N-(N-ethyl-3-piperidinyl)-2-bromo-9-xanthenylamine.

EXAMPLE 11

A mixture of 5 g. of N-(N-ethoxycarbonyl-4-piperidinyl)-9-xanthenylamine, prepared as in Example 14, and 25 g. of potassium hydroxide in 125 ml. of aqueous ethanol is heated at reflux for three hours and then cooled and added with stirring to 1 liter of ice water. The mixture is extracted with ether and the extracts dried and concentrated in vacuo to give N-(4-piperidinyl)-9-xanthenylamine.

EXAMPLE 12

By the procedure of Example 2, using 1-ethyl-3-pyrrolidinone in place of 1-ethyl-3-piperidone, the product obtained as N-methyl-N-(N-ethyl-3-pyrrolidinyl)-9-xanthenylamine.

Similarly using 1-methyl-3-pyrrolidinone and 1-butyl-3-pyrrolidinone, the products obtained are N-methyl-(N-methyl-3-pyrrolidinyl)-9-xanthenylamine and N-methyl-N-(N-butyl-3-pyrrolidinyl)-9-xanthenylamine.

In the procedure of Example 2, using 1-ethyl-3-pyrrolidinone and ethylamine, the product obtained is N-ethyl-N-(N-ethyl-3-pyrrolidinyl-9-xanthenylamine. Using propylamine and butylamine, the products obtained are N-propyl-N-(N-ethy-3-pyrrolidinyl)-9-xanthenylamine and N-butyl-N-(N-ethyl-3-pyrrolidinyl)-9-xanthenylamine.

EXAMPLE 13

A mixture of 400 g. of ethyl acrylate (containing 0.75% hydroquinone inhibitor) and 114 g. of cyclopropylamine is heated in a bomb in an oil bath at 175° C. for 10 hours. The reaction mixture is then removed and distilled in vacuo to give N-cyclopropyl-N,N-di($\beta$-carbethoxyethyl)amine.

The above prepared diester (22.5 g.) is added to a vigorously stirred suspension of 24 g. of sodium hydride in 800 ml. of dry benzene under nitrogen. Absolute ethanol (1 ml.) is added, and then 202.2 g. of the above prepared diester is added at a rate to maintain a vigorous reflux. The mixture is heated at reflux for an additional 1.5 hours, then cooled in an ice bath, and treated stepwise with 70 g. of glacial acetic acid and then 60 ml. of water. The mixture is filtered and the filtrate distilled until only pure benzene distills over. The residual solution is concentrated in vacuo to give 1-cyclopropyl-3-carbethoxy-4-piperidone. The 1-cyclopropyl-3-carbethoxy-4-piperidone in aqueous solution is heated in a bomb at 185° C and distilled to give 1-cyclopropyl-4-piperidone.

To an ice cold solution of 2.8 g. of 1-cyclopropyl-4-piperidone in 300 ml. of absolute methanol is added 0.02 moles of a solution of hydrogen chloride-methanol, 27 g. of ammonium nitrate and 2.4 g. of sodium cyanoborohydride. The solution is stirred for 72 hours at 25° C. and then poured into dilute acetic acid. The acidic solution is washed with ether and then made basic by the addition of ammonium hydroxide. The basic solution is extracted with methylene chloride, and the organic extract dried. Concentration of the extract in vacuo gives 4-amino-1-cyclopropylpiperidine.

Refluxing 4-amino-1-cyclopropylpiperidine and 9-acetoxyxanthene in dry toluene for 24 hours, then working up as in Example 1 gives N-(N-cyclopropyl-4-piperidinyl)-9-xanthenylamine.

By the same procedure using cyclobutylamine and cyclopentylamine in place of cyclopropylamine, the products are N-(N-cyclobutyl-4-piperidinyl)-9-xanthenylamine and N-(N-cyclopentyl-4-piperidinyl)-9-xanthenylamine.

EXAMPLE 14

By the procedure of Example 13, 1-acetyl-3-piperidone is converted, using sodium cyanoborohydride, to 1-acetyl-4-aminopiperidine.

Refluxing 1-acetyl-3-aminopiperidine with 9-acetoxyxanthene in dry toluene by the procedure of Example 1 gives N-(N-acetyl-3-piperidinyl)-9-xanthenylamine.

Similarly, converting 1-ethoxycarbonyl-4-piperidone to 1-ethoxycarbonyl-4-aminopiperidine and then reacting wit 9-acetoxyxanthene, the product is N-(N-ethoxycarbonyl-4-piperidinyl)-9-xanthenylamine.

By the same procedure, 1-carbamoyl-4-piperidone (prepared by heating 4-piperidone hydrochloride with sodium cyanate in acetic acid) is reacted with sodium cyanoborohydride and the resulting 1-carbamoyl-4-aminopiperidine is converted to n-(N-carbamoyl-4-piperidinyl)-9-xanthenylamine.

EXAMPLE 15

An aqueous solution of 46 g. of allylamine hydrochloride, 15 g. of formaldehyde (as a 37% aqueous solution) and 32.5 g. of potassium cyanide under carbon dioxide is allowed to react at 5° C. for 30 minutes and then permitted to warm to 25° C. over three hours. The solution is extracted with ether. The extract is concentrated and the residue refluxed with a solution of ethanolic hydrochloride acid for four hours. This suspension is filtered and the filtrate concentrated to give N-allylglycine ethyl ester hydrochloride. This material is dissolved in chloroform and treated at 0° C. with a solution of ammonia-chloroform. The mixture is filtered and the filtrate concentrated. The residue is distilled in vacuo to give the N-allylglycine ethyl ester.

To 97 g. of N-allylglycine ethyl ester is added, with cooling, 66 g. of ethyl 4-bromobutyrate. After three days at 25° C., the mixture is filtered and the filtrate distilled in vacuo to give N-allyl-N-carboxymethyl-4-aminobutyric acid diethyl ester.

The above prepared diester (2.4 g.) is added to a vigorously stirred suspension of 2.4 g. of sodium hydride in 80 ml. of dry benzene under nitrogen. Absolute ethanol (0.1 ml.) is added and then 21.9 g. of the above prepared diester is added at a rate to maintain a vigorous reflux. The mixture is heated at reflux for an additional 1.5 hours, then cooled in an ice bath and treated stepwise with 7.0 g. of glacial acetic acid and then 6.0 ml. of water. The mixture is filtered and the filtrate distilled until only pure benzene distills over. The residual solution is diluted with ether and hydrogen chloride gas is bubbled through to precipitate the hydrochloride salt of 1-allyl-4-carboethoxy-3-piperidone. The salt is filtered off and refluxed for three hours in 20% hydrochloric acid and the mixture is evaporated to dryness at 10 mm. pressure. The solid is heated at 100° C. at 0.1 mm. for four hours, dissolved in water and solid potassium hydroxide is added to free the base. Potassium carbonate is added to the aqueous solution and then it is extracted with ether. The ether layer is dried over sodium sulfate and distilled in vacuo to give 1-allyl-3-piperidone.

1-Allyl-3-piperidone is converted to 1-allyl-3-aminopiperidine by the procedure of Example 13.

Refluxing 1-allyl-3-aminopiperidine and 9-acetoxyxanthene in dry toluene for 24 hours and working up by the procedure of Example 1 gives N-(N-allyl-3-piperidinyl)-9-xanthenylamine.

EXAMPLE 16

Using propargylamine hydrochloride in place of allylamine hydrochloride in the procedure of Example 15, the product obtained is N-(N-propargyl-3-piperidinyl)-9-xanthenylamine.

Similarly using the hydrochloride salts of the following amines:
  butylamine
  isobutylamine
  isopropylamine
the products are, respectively:
  N-(N-butyl-3-piperidinyl)-9-xanthenylamine
  N-(N-isobutyl-3-piperidinyl)-9-xanthenylamine.
  N-(N-isopropyl-3-piperidinyl)-9-xanthenylamine.

EXAMPLE 17

To 99 g. of cyclohexylamine at reflux temperature is added 115.5 g. of 1,4-dibromo-2-butanol at a rate which maintains reflux without external heating. The temperature of the reaction mixture is maintained at 130°–140° C. in an oil bath for two hours after addition is complete. Water (100 ml.) is added and this mixture is then acidified with concentrated hydrochloric acid, cooled and extracted with ether. The aqueous layer is made alkaline with 50% aqueous sodium hydroxide solution, saturated with solid potassium carbonate and extracted three times with chloroform. The combined chloroform extracts are dried over potassium carbonate, concentrated and the residue distilled in vacuo to give N-cyclohexyl-3-pyrrolidinol.

To a stirred solution of 169 g. of N-cyclohexyl-3-pyrrolidinol in 600 ml. of chloroform, acidified with gaseous hydrogen chloride, is added 130 g. of thionyl chloride. This solution is refluxed for four hours, then poured onto ice water and made basic with sodium carbonate. The organic layer is dried over sodium sulfate, concentrated, and the residue distilled in vacuo to give N-cyclohexyl-3-chloropyrrolidine.

A rapidly stirred suspension of 160 g. of N-cyclohexyl-3-chloropyrrolidine, 148 g. of potassium phthalimide and 700 ml. of dimethyl sulfoxide is heated at 110°–113° C. for 16 hours and filtered while hot. Water is added and the precipitate is filtered off, washed with water, air-dried and recrystallized from iso-octane-benzene to give 1-cyclohexyl-3-phthalimidopyrrolidine.

A mixture of 30 g. of the above prepared phthalimidopyrrolidine 5.5 g. of hydrazine hydrate (in 85% solution) and 100 ml. of 95% aqueous ethanol is heated for two hours at reflux, cooled and then treated with concentrated hydrochloric acid until the solution is acidic. The mixture is filtered, the solid washed with 95% aqueous ethanol, and the combined filtrates are concentrated to 50 ml. An equal volume of water is added, and the solution is filtered. The filtrate is evaporated to dryness in vacuo and the residue treated with 10% aqueous sodium hydroxide solution and methylene chloride. The aqueous phase is saturated with sodium carbonate and the organic layer is separated, dried over solid sodium hydroxide and concentrated to give the N-cyclohexyl-3-aminopyrrolidine.

Refluxing N-cyclohexyl-3-aminopyrrolidine with 9-acetoxyxanthene in dry toluene for 24 hours, then working up as in Example 1 gives N-(N-cyclohexyl-3-pyrrolidinyl)-9-xanthenylamine.

By the same procedure using cyclobutylamine, N-(N-cyclobutyl-3-pyrrolidinyl)-9-xanthenylamine is obtained.

EXAMPLE 18

By the procedure of Example 17, using the following amines in place of cyclohexylamine:
  aniline
  benzylamine
  allylamine
  propargylamine
the products are respectively:
  N-(N-phenyl-3-pyrrolidinyl)-9-xanthenylamine
  N-(N-benzyl-3-pyrrolidinyl)-9-xanthenylamine
  N-(N-allyl-3-pyrrolidinyl)-9-xanthenylamine
  N-(N-propargyl-3-pyrrolidinyl)-9-xanthenylamine.

EXAMPLE 19

By the procedure of Example 1, using the following substituted xanthydrols in place of xanthydrol:
  3-methylxanthydrol
  2-methylxanthydrol
  2-ethylxanthydrol
  2-t-butylxanthydrol
  3-methoxyxanthydrol
  2-ethoxyxanthydrol
the products obtained are, respectively:
  N-(N-ethyl-3-piperidinyl)-3-methyl-9-xanthenylamine
  N-(N-ethyl-3-piperidinyl)-2-methyl-9-xanthenylamine
  N-(N-ethyl-3-piperidinyl)-2-ethyl-9-xanthenylamine
  N-(N-ethyl-3-piperidinyl)-2-t-butyl-9-xanthenylamine
  N-(N-ethyl-3-piperidinyl)-3-methoxy-9-xanthenylamine
  N-(N-ethyl-3-piperidinyl)-2-ethoxy-9-xanthenylamine.

By the same procedure, using 3-amino-1-ethylpyrrolidine in place of 3-amino-1-ethyl-piperidine and using the above listed substituted xanthydrols, the corresponding N-(N-ethyl-3-pyrrolidinyl-(substituted)-9-xanthenylamines are obtained.

EXAMPLE 20

In the procedure of Example 1, using in place of xanthydrol the following:
  2,7-dibromomoxanthydrol
  1,7-dimethoxyxanthydrol
  1,8-dimethylxanthydrol
the products are, respectively:
  N-(N-ethyl-3-piperidinyl)-2,7-dibromo-9-xanthenylamine
  N-(N-ethyl-3-piperidinyl)-1,7-dimethoxy-9-xanthenylamine
  N-(N-ethyl-3-piperidinyl)-1,8-dimethyl-9-xanthenylamine.

EXAMPLE 21

A suspension of 25 g. of 3-chloro-6-methoxyxanthone in 175 ml. of 95% aqueous ethanol is poured into a flask containing sodium amalgam prepared from 9.0 g. of sodium and 55 ml. of mercury. The flask is stoppered and shaken vigorously for 20 minutes with intermittant venting. The amalgam is then allowed to settle and the ethanolic supernatant is decanted into 1.5 liters of water. The precipitate is filtered from the resulting mixture, washed with water, and air dried to yield 3-chloro-6-methoxyxanthydrol.

Using 3-chloro-6-methoxyxanthydrol in place of xanthydrol in the procedure of Example 1 gives N-(N- ethyl-3-piperidinyl)-3-chloro-6-methoxyxanthenylamine.

Similarly, using the following xanthones as starting materials:
2-propylxanthone
3,6-dichloroxanthone
3-methoxy-6-methylxanthone
6-methoxy-2-methylxanthone
3-hydroxyxanthone
2-hydroxyxanthone
6-hydroxy-2-methylxanthone
the products are, respectively:
N-(N-ethyl-3-piperidinyl)-2-propylxanthenylamine
N-(N-ethyl-3-piperidinyl)-3,6-dichloroxanthenylamine
N-(N-ethyl-3-piperidinyl)-3-methoxy-6-methylxanthenylamine
N-(N-ethyl-3-piperidinyl)-6-methoxy-2-methylxanthenylamine
N-(N-ethyl-3-piperidinyl)-3-hydroxyxanthenylamine
N-(N-ethyl-3-piperidinyl)-2-hydroxyxanthenylamine
N-(N-ethyl-3-piperidinyl)-6-hydroxy-2-methylxanthenylamine

EXAMPLE 22

By the procedure of Example 15, using in place of allylamine hydrochloride the hydrochlorides of the following amines:
cyclohexylamine
cyclopentylamine
cyclobutylamine
the products obtained are, respectively:
N-(N-cyclohexyl-3-piperidinyl)-9-xanthenylamine
N-(N-cyclopentyl-3-piperidinyl)-9-xanthenylamine
N-(N-cyclobutyl-3-piperidinyl)-9-xanthenylamine.

EXAMPLE 23

An aqueous solution of 46 g. of cyclopropylamine hydrochloride, 15 g. of formaldehyde (as a 37% aqueous solution) and 32.5 g. of potassium cyanide under carbon dioxide is allowed to react at 5° C. for 30 minutes and then permitted to warm to 25° C. over three hours. The solution is extracted with ether. The extract is concentrated. The residue is refluxed with a solution of 87 g. of barium hydroxide in 800 ml. of 1:1 methanol-water for five hours. This solution is concentrated in vacuo and the residual salt is dissolved in methanol. The methanolic solution at 0° C. is acidified to pH 5 with hydrogen chloride-methanol and treated with a solution of diazomethane in ether. The solution is concentrated in vacuo, and the residue is triturated with ether. The ethereal phase is dried, filtered and concentrated. The residual oil is distilled in vacuo to give the N-cyclopropylglycine methyl ester.

The above prepared ester is reacted with methyl 4-bromobutyrate by the procedure of Example 15 to give N-cyclopropyl-N-carboxymethyl-4-butyric acid dimethyl ester.

Using the above prepared diester in place of the diester of Example 13 in the procedure of that example gives N-(N-cyclopropyl-3-piperidinyl)-9-xanthenylamine.

EXAMPLE 24

A solution of 18.9 g. of 1-benzyl-3-piperidone in 150 ml. of absolute alcohol at 0° C. is treated with hydrogen chloride gas and then refluxed for one hour. The solvent is removed in vacuo and the residue treated with cold 5% aqueous sodium bicarbonate solution and ether. The ether solution is dried and concentrated in vacuo to give 1-benzyl-3,3-diethoxypiperidine.

A mixture of 15 g. of 1-benzyl-3,3-diethoxypiperidine in 100 ml. of absolute alcohol and 0.5 g. of 10% palladium on charcoal is shaken over 50 p.s.i. of hydrogen at 50° C. for six hours. The catalyst is filtered and washed with ethanol. The solvent is removed by distillation to give 3,3-diethoxypiperidine.

A solution of 8.7 g. of 3,3-diethoxypiperidine in 100 ml. of dry chloroform is treated at 0° C. with 5 g. of triethylamine followed by 5.4 g. of ethyl chloroformate. After stirring at 25° C. for two hours, the solvent is removed in vacuo. The residue is extracted with ether and the extract concentrated in vacuo. This residue is treated with dilute hydrochloric acid for two hours. The solution is then saturated with sodium chloride and extracted with chloroform. The chloroform extract is washed with 5% aqueous sodium bicarbonate solution, dried and concentrated in vacuo to give 1-carbethoxy-3-piperidone.

By the procedure of Example 13, 1-carbethoxy-3-piperidone is converted, using sodium cyanoborohydride, to 3-amino-1-carbethoxypiperidine.

A mixture of 3-amino-1-carbethoxypiperidine and 9-acetoxyxanthene in dry toluene is refluxed by the procedure of Example 1 to give N-(N-ethoxycarbonyl-3-piperidinyl)-9-xanthenylamine.

Similarly, in the above procedure using, in place of ethyl chloroformate, the following:
methyl chloroformate
butyl chloroformate
propionyl chloride
butyryl chloride
the products are, respectively:
N-(N-methoxycarbonyl-3-piperidinyl)-9-xanthenylamine
N-(N-butoxycarbonyl-3-piperidinyl)-9-xanthenylamine
N-(N-propionyl-3-piperidinyl)-9-xanthenylamine
N-(N-butyryl-3-piperidinyl)-9-xanthenylamine.

By the above procedure, using 3-amino-1-carbamoyl-piperidine (prepared by heating 3,3-diethoxypiperidine with sodium cyanate in acetic acid and treating the resulting 1-carbamoyl-3-piperidone with sodium cyanoborohydride by the procedure of Example 13), the product is N-(N-carbamoyl-3-piperidinyl)-9-xanthenylamine.

EXAMPLE 25

To a solution of 1.1 g. of N-(N-ethyl-3-piperidinyl)-9-xanthenylamine in 8 ml. of tetrahydrofuran and 50 ml. of diethyl ether at −5° C. was added 538 mg. of levo tartaric acid in 32 ml. of tetrahydrofuran. The resulting precipitate was allowed to stand one hour, filtered off, washed twice with 100 ml. portions of ether and air-dried to give N-(N-ethyl-3-piperidinyl)-9-xanthenylamine, tartrate, hydrate m.p. 146°–148° C. (dec.)

EXAMPLE 26

Reacting N-(N-ethyl-3-piperidinyl)-9-xanthenylamine with hydrogen chloride in ether at −10° C. gives the hydrochloride salt.

Also, reacting with concentrated sulfuric acid in ether gives N-(N-ethyl-3-piperidinyl)-9-xanthenylamine sulfate.

EXAMPLE 27

A mixture of 10 g. of 3-aminopiperidine and 29.6 g. of phthalic anhydride is heated at 150° C. for 30 minutes. This mixture which contains 1-(2-carboxybenzoyl)-3-phthalimidopiperidine is heated at reflux with 500 ml. of 6N hydrochloric acid for two hours. The aqueous phase is extracted with ether and then concentrated in vacuo. The residue is extracted with dilute aqueous sodium hydroxide solution and methylene chloride. The organic phase is dried and concentrated in vacuo to give 3-phthalimidopiperidine.

A mixture of 11.5 g. of 3-phthalimidopiperidine and 2.85 g. of methyl isocyanate in 100 ml. of dry benzene is stirred at 25° C. for 2 hours. The resulting mixture is concentrated in vacuo and filtered to give 1-(N-methylcarbamoyl)-3-phthalimidopiperidine. Treating this phthalimidopiperidine with hydrazine hydrate by the procedure of Example 17 gives 1-(N-methylcarbamoyl)-3-aminopiperidine.

Reacting 1-(N-methylcarbamoyl)-3-aminopiperidine with 9-acetoxyxanthene in dry toluene by the procedure of Example 1 gives N-[1-(N-methylcarbamoyl)-3-piperidinyl]-9-xanthenylamine.

By the same procedure, using ethyl isocyanate the corresponding N-ethylcarbamoyl compound is prepared. Similarly, using butyl isocyanate, the corresponding N-butylcarbamoyl compound is prepared.

In addition, reacting 3-phthalimidopiperidine with N,N-dimethylcarbamoyl chloride and treating the resulting 1-(N,N-dimethylcarbamoyl)-3-phthalimidopiperidine with hydrazine hydrate gives 1-(N,N-dimethylcarbamoyl)-3-aminopiperidine. Reacting this piperidine compound with 9-acetoxyxanthene by the procedure of Example 1 gives N-[1-(N,N-dimethylcarbamoyl)-3-piperidinyl]-9-xanthenylamine.

Similarly, using N,N-dimethylcarbamoyl chloride and N,N-dibutylcarbamoyl chloride, the products are N-[1-(N,N-diethylcarbamoyl)-3-piperidinyl]-9-xanthenylamine and N-[1-(N,N-dibutylcarbamoyl)-3-piperidinyl]-9-xanthenylamine, respectively.

EXAMPLE 28

| Ingredients | Amounts |
| --- | --- |
| N-(N-Ethyl-3-piperidinyl)-9-xanthenylamine | 200 mg. |
| Lactose | 75 mg. |
| Magnesium stearate | 5 mg. |

The ingredients are mixed and filled into a hard gelatin capsule.

EXAMPLE 29

| Ingredients | Amounts |
| --- | --- |
| N-Methyl-N-(N-ethyl-3-piperidinyl)-9-xanthenylamine | 150 mg. |

EXAMPLE 29-continued

| Ingredients | Amounts |
| --- | --- |
| Peanut oil | 100 mg. |

The ingredients are mixed and filled into a soft gelatin capsule.

EXAMPLE 30

| Ingredients | Amounts |
| --- | --- |
| N-(N-Methyl-4-piperidinyl-9-xanthenylamine | 100 mg. |
| Lactose | 75 mg. |

The ingredients are mixed and filled into a hard gelatin capsule.

What is claimed is:

1. A compound of the formula:

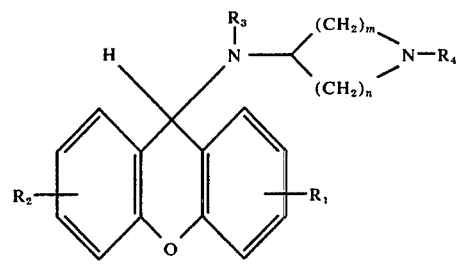

in which:
   $R_1$ is hydrogen, halogen, hydroxy, lower alkyl or lower alkoxy;
   $R_2$ is hydrogen, halogen, lower alkyl or lower alkoxy;
   $R_3$ is hydrogen or lower alkyl;
   $R_4$ is hydrogen, lower alkyl, allyl, propargyl, cycloalkyl having 3 to 6 carbon atoms, lower alkanoyl, lower alkoxycarbonyl, carbamoyl, N-lower alkylcarbamoyl, N,N-di- lower alkylcarbamoyl, phenyl or benzyl;
   $m$ is 1 or 2 and $n$ is 2 or 3, the sum of $m$ and $n$ being 3 or 4 or a pharmaceutically acceptable acid addition salt thereof.

2. A compound of claim 1 in which $R_1$ and $R_2$, being the same or different, are hydrogen, chloro, methyl or methoxy.

3. A compound of claim 1 in which $R_1$ and $R_2$ are hydrogen, $R_3$ is hydrogen or methyl and $R_4$ is methyl or ethyl.

4. A compound of claim 1 said compound being N-(N-ethyl-3-piperidinyl)-9-xanthenylamine.

5. A pharmaceutical composition having gastric acid secretion inhibitory activity comprising a pharmaceutical carrier and an effective amount of a compound of claim 1.

6. A method of inhibiting gastric acid secretion comprising administering to an animal an effective amount of a compound of claim 1.

* * * * *